(12) United States Patent
Nordberg et al.

(10) Patent No.: US 10,416,046 B2
(45) Date of Patent: Sep. 17, 2019

(54) DEVICE, SYSTEM, AND METHOD FOR SELECTING A TARGET ANALYTE

(71) Applicant: RareCyte, Inc., Seattle, WA (US)

(72) Inventors: Joshua Nordberg, Bainbridge Island, WA (US); Steve Quarre, Woodinville, WA (US); Ronald Seubert, Sammamish, WA (US)

(73) Assignee: RareCyte, Inc., Seattle, WA (US)

( * ) Notice: Subject to any disclaimer, the term of this patent is extended or adjusted under 35 U.S.C. 154(b) by 0 days.

(21) Appl. No.: 15/621,896

(22) Filed: Jun. 13, 2017

(65) Prior Publication Data
US 2017/0276575 A1 Sep. 28, 2017

Related U.S. Application Data

(63) Continuation-in-part of application No. 15/275,416, filed on Sep. 25, 2016, now Pat. No. 9,810,605, which is a continuation of application No. 14/248,510, filed on Apr. 9, 2014, now Pat. No. 9,519,002.

(60) Provisional application No. 61/922,931, filed on Jan. 2, 2014, provisional application No. 61/810,834, filed on Apr. 11, 2013.

(51) Int. Cl.
*G01N 1/14* (2006.01)
*G01N 35/10* (2006.01)
*B01L 3/02* (2006.01)
*C12M 1/26* (2006.01)
*G01N 35/00* (2006.01)
*G01N 15/10* (2006.01)

(52) U.S. Cl.
CPC .............. *G01N 1/14* (2013.01); *B01L 3/0217* (2013.01); *C12M 33/04* (2013.01); *G01N 35/0098* (2013.01); *G01N 35/1009* (2013.01); *G01N 35/1011* (2013.01); *B01L 2200/0657* (2013.01); *B01L 2200/0668* (2013.01); *B01L 2300/14* (2013.01); *B01L 2400/043* (2013.01); *B01L 2400/0478* (2013.01); *B01L 2400/0487* (2013.01); *G01N 2001/1454* (2013.01); *G01N 2015/1006* (2013.01); *G01N 2015/1081* (2013.01)

(58) Field of Classification Search
None
See application file for complete search history.

(56) References Cited

U.S. PATENT DOCUMENTS

| 2,610,541 | A | | 9/1952 | Rowland |
| 3,915,651 | A | | 10/1975 | Nishi |
| 3,991,616 | A | | 11/1976 | Stahli |
| 4,519,258 | A | | 5/1985 | Jakubowicz |
| 4,542,277 | A | | 9/1985 | Cecil |
| 4,830,832 | A | * | 5/1989 | Arpagaus .............. B01L 3/0217 422/509 |
| 4,917,274 | A | | 4/1990 | Asa et al. |

(Continued)

FOREIGN PATENT DOCUMENTS

| JP | 2012522610 A | 9/2012 |
| WO | WO2010098549 A2 | 9/2010 |

*Primary Examiner* — Jill A Warden
*Assistant Examiner* — Brittany I Fisher
(74) *Attorney, Agent, or Firm* — Shay Glenn LLP

(57) ABSTRACT

This disclosure is directed to a device and a system for picking a target analyte of a suspension. A picker introduces at least one force, such as by a magnetic gradient and/or by a pressure gradient, to extract the target analyte from a sample.

21 Claims, 12 Drawing Sheets

(56) References Cited

U.S. PATENT DOCUMENTS

| | | | | |
|---|---|---|---|---|
| 5,125,748 A | * | 6/1992 | Bjornson | G01N 21/253 356/414 |
| 5,139,744 A | * | 8/1992 | Kowalski | G01N 21/253 422/63 |
| 5,289,948 A | | 3/1994 | Moss et al. | |
| 5,468,453 A | | 11/1995 | Holt et al. | |
| 5,516,564 A | | 5/1996 | Root et al. | |
| 5,525,302 A | | 6/1996 | Astle | |
| 5,639,426 A | * | 6/1997 | Kerr | B01L 3/0275 422/501 |
| 5,705,814 A | * | 1/1998 | Young | G01Q 30/06 250/307 |
| 5,743,960 A | | 4/1998 | Tisone | |
| 6,063,339 A | | 5/2000 | Tisone et al. | |
| 6,199,435 B1 | | 3/2001 | Wilmer et al. | |
| 6,254,832 B1 | * | 7/2001 | Rainin | B01L 3/0227 422/518 |
| 6,283,329 B1 | | 9/2001 | Bezaire et al. | |
| 6,354,479 B1 | | 3/2002 | Reiber et al. | |
| 6,440,370 B1 | | 8/2002 | Blum et al. | |
| 6,565,728 B1 | | 5/2003 | Kozulic | |
| 6,702,990 B1 | | 3/2004 | Camacho et al. | |
| 6,806,595 B2 | | 10/2004 | Quarre | |
| 7,033,543 B1 | | 4/2006 | Panzer et al. | |
| 7,343,724 B1 | | 3/2008 | Williams et al. | |
| 8,043,865 B2 | | 10/2011 | Karg et al. | |
| 8,263,390 B2 | | 9/2012 | Tajima | |
| 8,524,170 B2 | | 9/2013 | Petrek | |
| 8,871,157 B2 | | 10/2014 | Homberg et al. | |
| 9,810,605 B2 | | 11/2017 | Nordberg et al. | |
| 2001/0047692 A1 | | 12/2001 | Lipscomb et al. | |
| 2002/0134175 A1 | | 9/2002 | Mehra et al. | |
| 2002/0153909 A1 | | 10/2002 | Petersen et al. | |
| 2003/0039589 A1 | | 2/2003 | Smith | |
| 2003/0165408 A1 | | 9/2003 | Takeda et al. | |
| 2003/0223910 A1 | | 12/2003 | Jackson et al. | |
| 2005/0016921 A1 | | 1/2005 | Gjerde et al. | |
| 2005/0056713 A1 | | 3/2005 | Tisone et al. | |
| 2005/0173458 A1 | | 8/2005 | Hiranaga et al. | |
| 2006/0183217 A1 | | 8/2006 | Yanagida et al. | |
| 2007/0180935 A1 | | 8/2007 | Angus et al. | |
| 2008/0083268 A1 | | 4/2008 | Hammami et al. | |
| 2008/0182340 A1 | * | 7/2008 | Lemmo | B01L 3/0289 436/180 |
| 2008/0227663 A1 | | 9/2008 | Tisone et al. | |
| 2008/0296157 A1 | | 12/2008 | Bauer et al. | |
| 2009/0017554 A1 | | 1/2009 | Vann | |
| 2009/0095825 A1 | | 4/2009 | Ahmadi et al. | |
| 2009/0148527 A1 | | 6/2009 | Robinson et al. | |
| 2009/0177192 A1 | | 7/2009 | Rioux et al. | |
| 2009/0202392 A1 | | 8/2009 | Urano et al. | |
| 2010/0043575 A1 | | 2/2010 | Tajima | |
| 2010/0119416 A1 | | 5/2010 | Tajima | |
| 2010/0140182 A1 | | 6/2010 | Chapman et al. | |
| 2010/0323372 A1 | | 12/2010 | Fulton et al. | |
| 2011/0027149 A1 | * | 2/2011 | Uldry | B01L 3/0217 422/501 |
| 2011/0038769 A1 | | 2/2011 | Gjerde et al. | |
| 2011/0182782 A1 | * | 7/2011 | Dzuong | B01L 3/0217 422/501 |
| 2011/0300035 A1 | | 12/2011 | Taniguchi et al. | |
| 2012/0091008 A1 | | 4/2012 | Muir et al. | |
| 2012/0121482 A1 | | 5/2012 | Ochman et al. | |
| 2012/0291567 A1 | | 11/2012 | Homberg et al. | |
| 2012/0291872 A1 | | 11/2012 | Brady et al. | |
| 2013/0026191 A1 | * | 1/2013 | Duquet | B01L 3/0265 222/256 |
| 2013/0074614 A1 | | 3/2013 | Holmes et al. | |
| 2014/0219887 A1 | | 8/2014 | Sheldon | |

\* cited by examiner

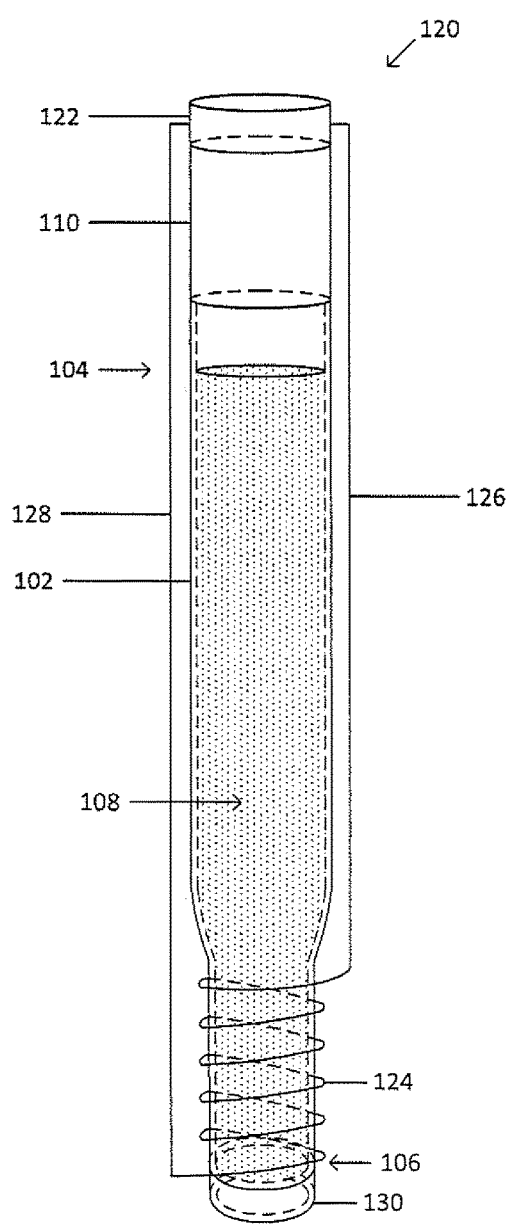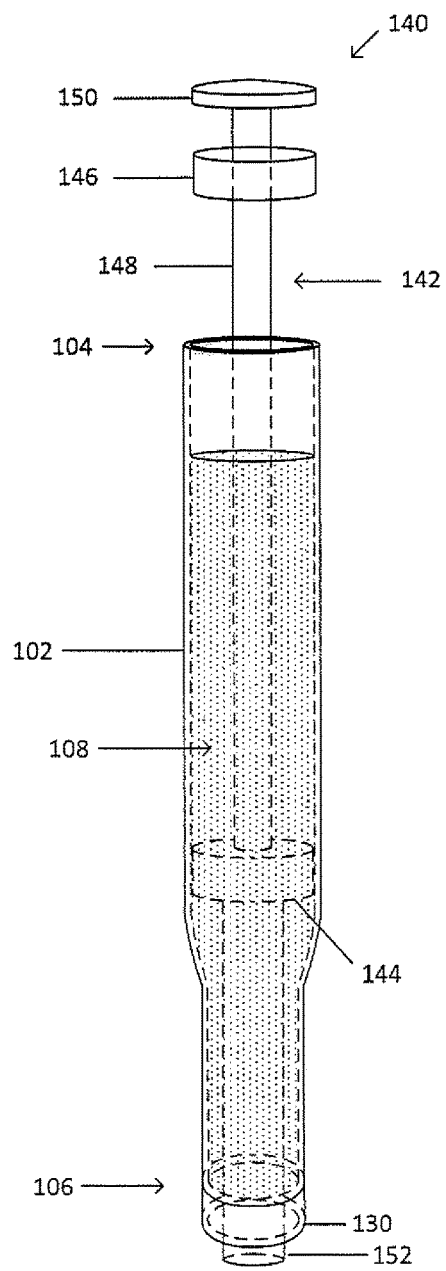
Fig. 1C
Fig. 1D

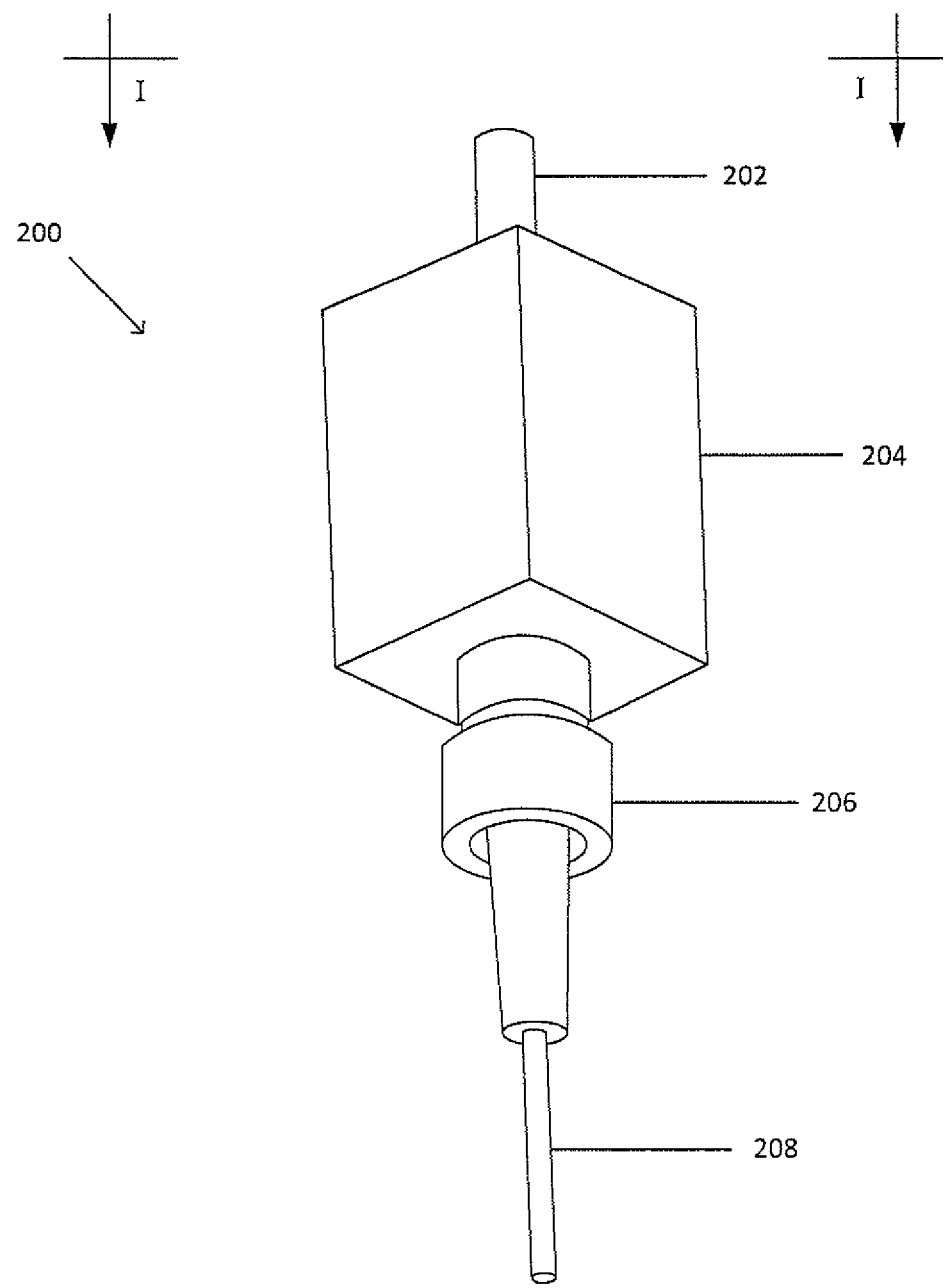

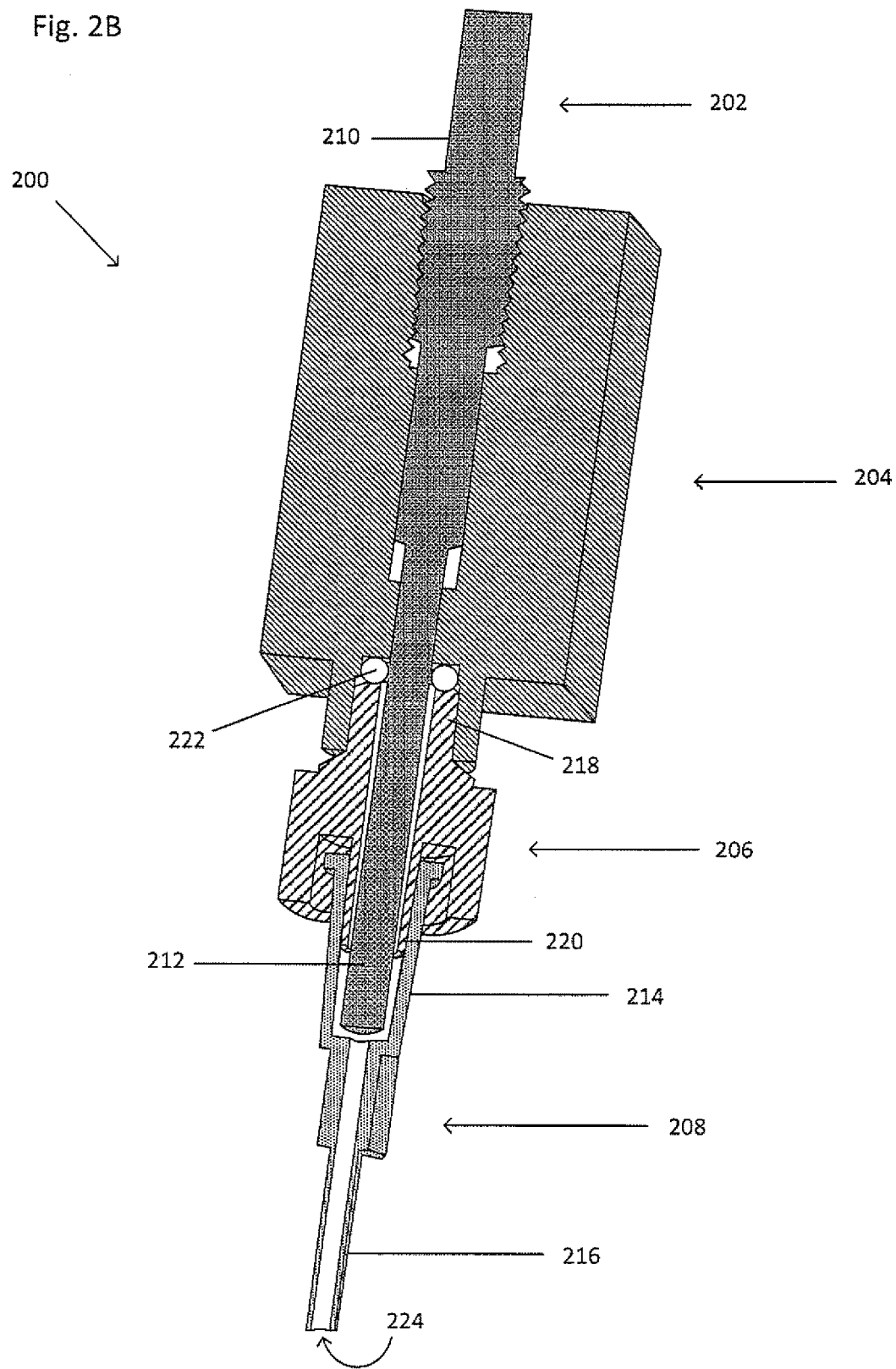

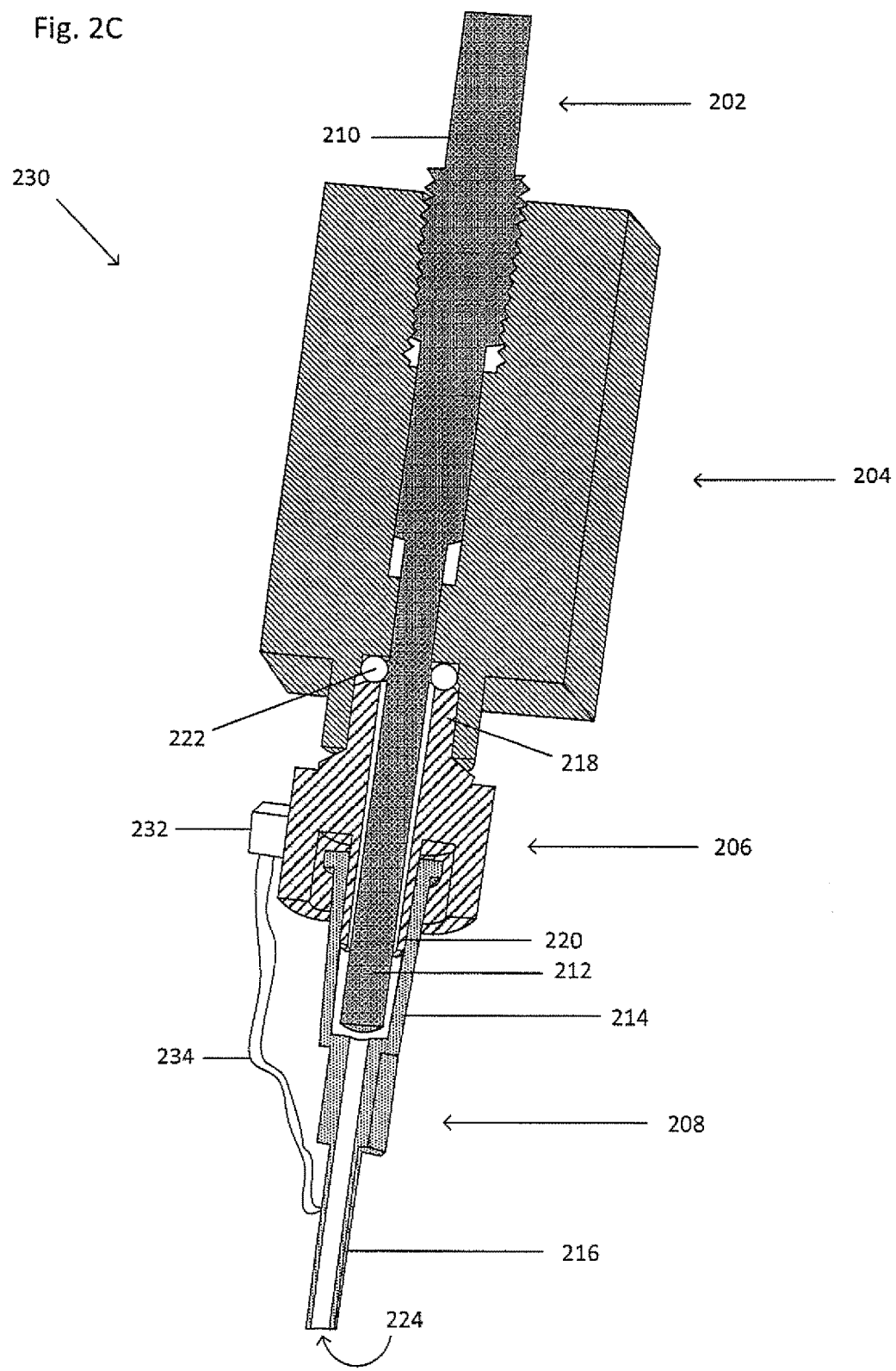

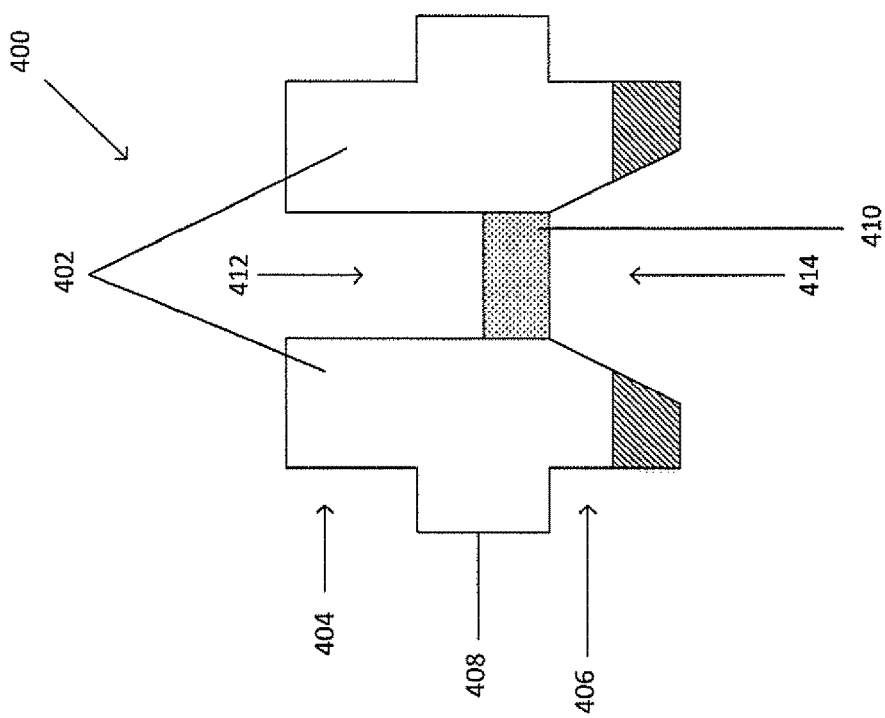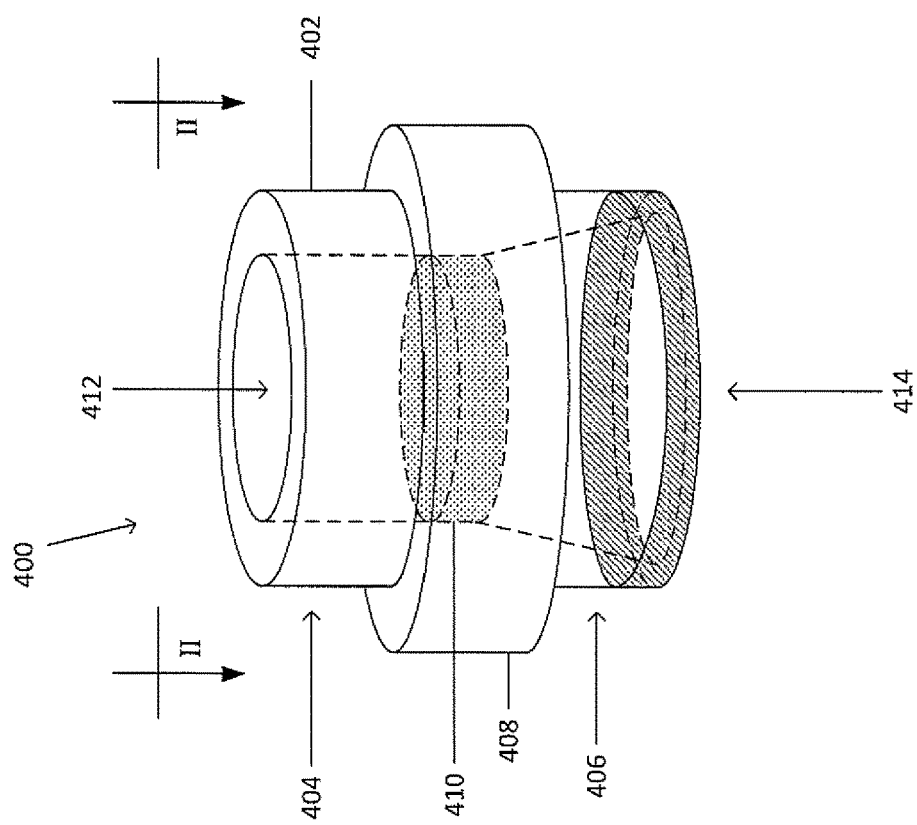

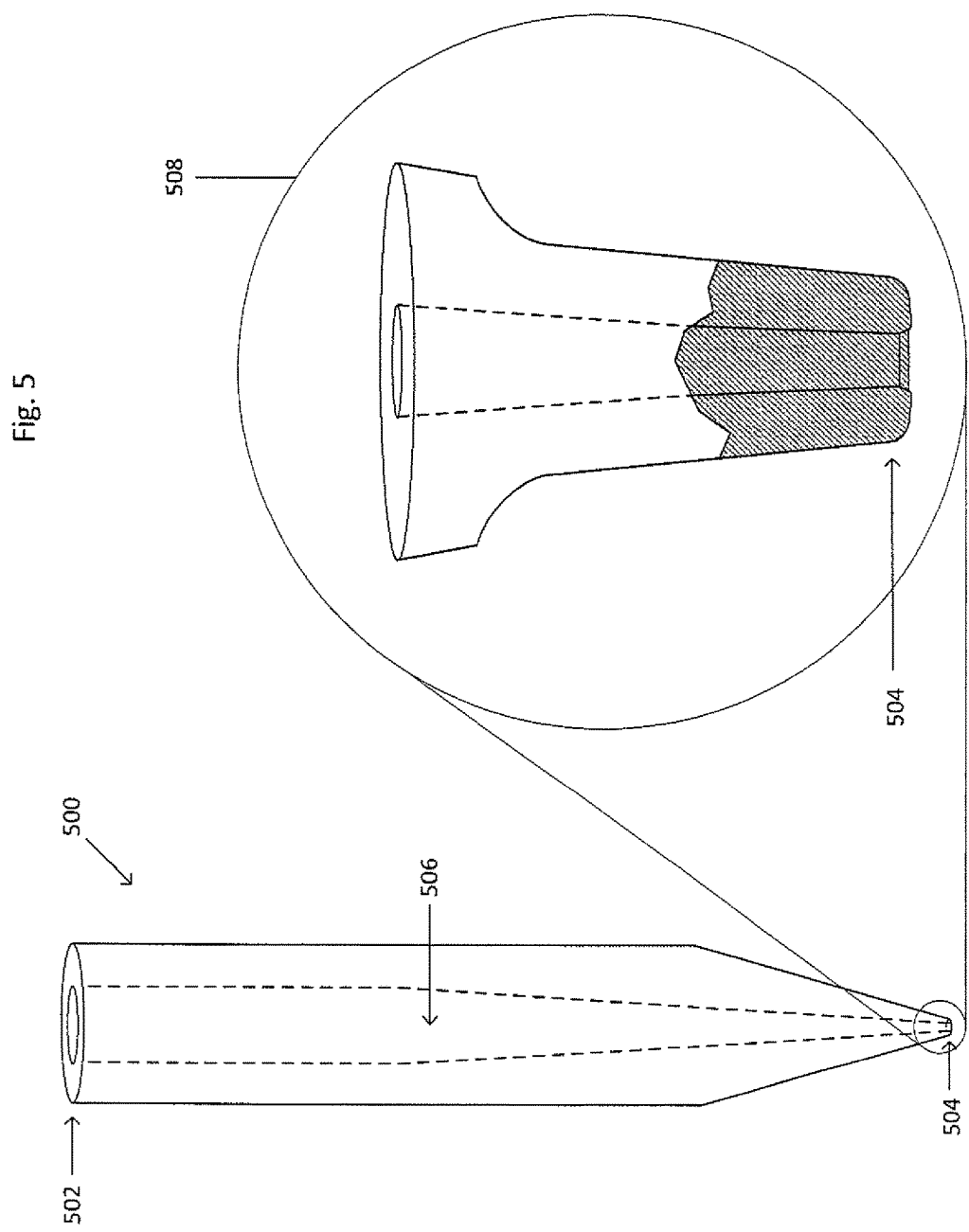

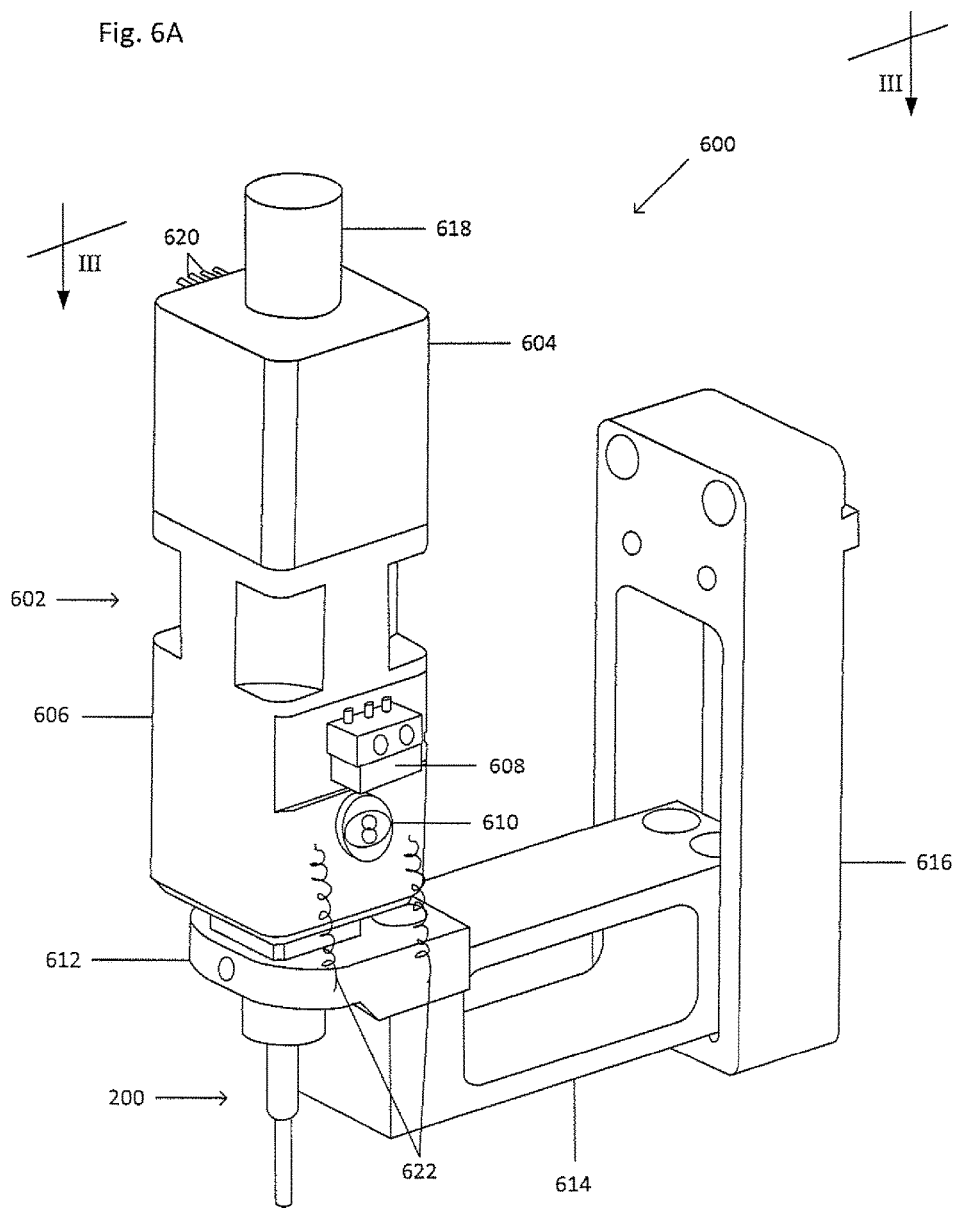

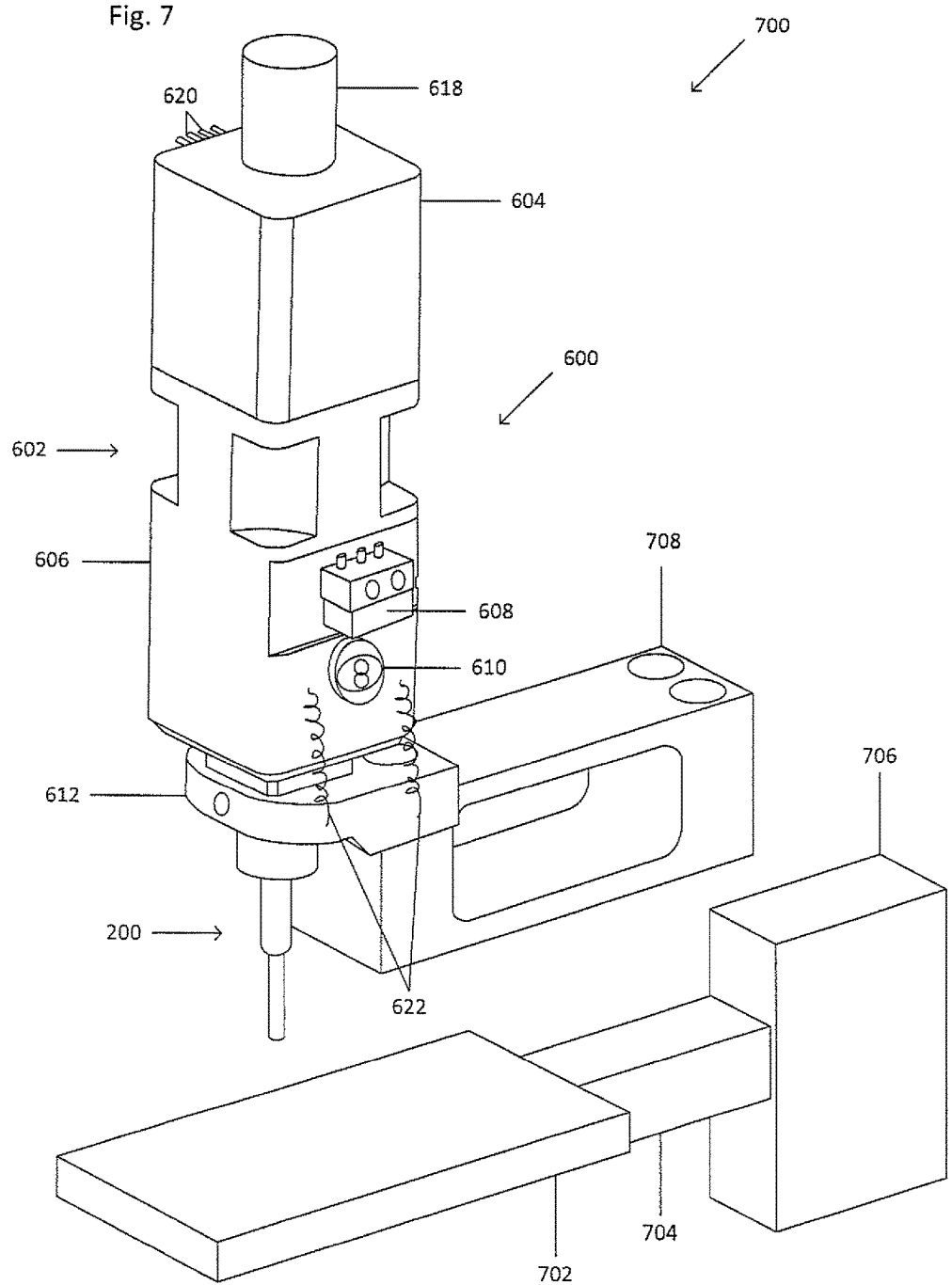

DEVICE, SYSTEM, AND METHOD FOR SELECTING A TARGET ANALYTE

CROSS-REFERENCE TO A RELATED APPLICATIONS

This application is a continuation-in-part of application Ser. No. 15/275,416, filed Sep. 25, 2016, which is a continuation of application Ser. No. 14/248,510, filed Apr. 9, 2014 (now U.S. Pat. No. 9,519,002, issued Dec. 13, 2016), which claims the benefit of Provisional Application No. 61/810,834, filed Apr. 11, 2013, and Provisional Application No. 61/922,931, filed Jan. 2, 2014.

TECHNICAL FIELD

This disclosure relates generally to micromanipulation of a target analyte, though more specifically, to picking and isolating the target analyte.

BACKGROUND

Suspensions often include materials of interest that are difficult to detect, extract and isolate for analysis. For instance, whole blood is a suspension of materials in a fluid. The materials include billions of red and white blood cells and platelets in a proteinaceous fluid called plasma. Whole blood is routinely examined for the presence of abnormal organisms or cells, such as fetal cells, endothelial cells, epithelial cells, parasites, bacteria, and inflammatory cells, and viruses, including HIV, cytomegalovirus, hepatitis C virus, and Epstein-Barr virus, and nucleic acids. Currently, practitioners, researchers, and those working with blood samples try to separate, isolate, and extract certain components of a peripheral blood sample for examination. Typical techniques used to analyze a blood sample include the steps of smearing a film of blood on a slide and staining the film in a way that enables certain components to be examined by bright field microscopy.

On the other hand, materials of interest composed of particles that occur in very low numbers are especially difficult if not impossible to detect and analyze using many existing techniques. Consider, for instance, circulating tumor cells ("CTCs"), which are cancer cells that have detached from a tumor, circulate in the bloodstream, and may be regarded as seeds for subsequent growth of additional tumors (i.e., metastasis) in different tissues. The ability to accurately detect and analyze CTCs is of particular interest to oncologists and cancer researchers, but CTCs occur in very low numbers in peripheral whole blood samples. For instance, a 7.5 ml sample of peripheral whole blood that contains as few as 3 CTCs is considered clinically relevant in the diagnosis and treatment of a cancer patient. However, detecting even 1 CTC in a 7.5 ml blood sample may be clinically relevant and is equivalent to detecting 1 CTC in a background of about 50 billion red and white blood cells. Using existing techniques to find, isolate and extract as few as 3 CTCs of a whole blood sample is extremely time consuming, costly and is extremely difficult to accomplish.

As a result, practitioners, researchers, and those working with suspensions continue to seek systems and methods to more efficiently and accurately detect, isolate and extract target materials of a suspension.

DESCRIPTION OF THE DRAWINGS

FIGS. 1A-1D show examples of a picker.
FIG. 2A-2B show an example picker.
FIG. 2C shows an example picker.
FIGS. 4A-4B show an example fluorescent picker tip.
FIG. 5 shows an example picker tip.
FIGS. 6A-6B show an example picking system.
FIG. 7 shows an example picking system

DETAILED DESCRIPTION

This disclosure is directed to a device and a system for picking a target analyte of a suspension. A picker introduces at least one force, such as by a magnetic gradient and/or by a pressure gradient, to extract the target analyte from a sample.

General Description of Slide and Picker Systems

Figure 1A:
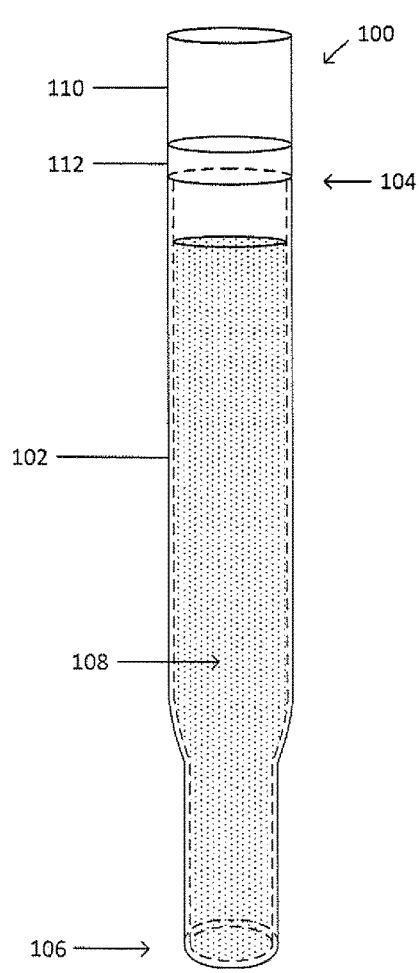

FIG. 1A shows an example picker 100. The picker 100 includes a main body 102, a back end 104, and a tip 106. The picker 100 may be solid or may be a hollow tube having an inner chamber for holding a liquid, target analyte, or any other appropriate material. When the picker 100 is a hollow tube, the picker 100 may also include a liquid 108 within the inner chamber of the picker 100, where the liquid may be a solution, a buffer, a ferrofluid, or the like. The picker 100 may be used to manipulate a target analyte. The target analyte may be manipulated, such as by moving, removal, or isolation, when the specific target analyte is in a vessel, such as a tube or a well, or on a slide. The target analyte can be isolated through the introduction of a force, thereby attracting or pulling the target analyte. The tip 106 engages the target analyte for moving, removal, or isolation. The force may be created with suction or a pressure gradient, such as a vacuum. The back end 104 may be connected to a pump 110, such as a vacuum pump, a lead screw, or a hand pump with a wheel, to aid in providing the force for moving, removal, or isolation. The picker 100 may also include a light source 112, such as an LED, to illuminate an area in which the target analyte may be present. The light source 112 may be located anywhere along the main body 102, including the back end 104 and the tip 106. When the light source 112 is located at the back end 104, the main body 102 may be composed of a material capable of propagating or transmitting a light signal produced by the light source 112, such that the light signal exits at the tip 106 to illuminate the desired area. The light source 112 may be connected to a power supply (not shown), such as a battery, to supply current or power.

Figure 1B:
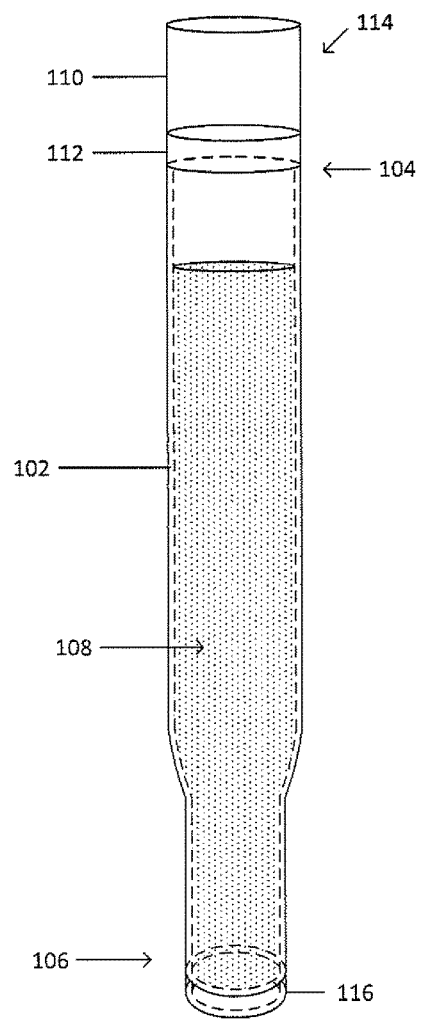

FIG. 1B shows an example picker 114. The picker 114 is similar to the picker 100, except that picker 114 includes a permanent magnet 116, such as a donut-shaped magnet. The permanent magnet 116 generates a magnetic field for attracting a particle of a target analyte-particle complex, a target analyte having been previously conjugated with the particle to form the target analyte-particle complex. The picker 114 may also include a magnetizable material to extend or transmit the magnetic field produced by the magnet. The permanent magnet 116 may be located at the tip 106 or at or near the back end 104. The permanent magnet 116 may be removable. Alternatively, the fluid, such as a ferrofluid, within the picker 114 may be used to generate the magnetic field or magnetic gradient.

FIG. 1C shows an example picker 120. The picker 120 is similar to the picker 100, except that picker 120 includes an electromagnet. The electromagnet includes a power source 122, a first lead 126, a second lead 128, and a coil 124. The power source 122 may be, but is not limited to, a battery, a DC supply, or an AC supply. The electromagnet generates a magnetic field for attracting a particle of a target analyte-particle complex, a target analyte having been previously conjugated with the particle to form the target analyte-particle complex. The picker 120 may be composed of a magnetizable material to extend or transmit the magnetic field produced by the magnet. The first lead 126, the second 128, and the coil 124 may be located outside of a wall of the picker 120, may be embedded with the wall of the picker 120, or may be located inside of the picker 120. The picker 120 may also include a light source 130, such as an LED, to illuminate an area in which the target analyte may be present. The light source 130 may be located anywhere along the main body 102, including the back end 104 and the tip 106. When the light source 130 is located at the back end 104, the main body 102 may be composed of a material capable of propagating or transmitting a light signal produced by the light source 130, such that the light signal exits at the tip 106 to illuminate the desired area. The light source 130 may be connected to a power supply (not shown), such as a battery, to supply current or power.

FIG. 1D shows an example picker 140. The picker 140 includes a retractable shaft 142, the retractable shaft 142 being thinner than the main body 102 and being extendable from the tip 106. The retractable shaft 142 can be located within the main body 102, can be extended out of the tip 106 to engage a target analyte, and can be retracted into the main body 102. When the target analyte attaches to the retractable shaft 142, the target analyte can be drawn into the main body 102. The retractable shaft 142 may include an engagement portion 152, a stopper 144, a grip 150, and a rod 148. The engagement portion 152 may be extended out of the tip 106 to engage the target analyte. The stopper 144 may be sized to fit within the main body 102, but be larger than the tip 106 or a taper from the main body 102 to the tip 106, thereby preventing the retractable shaft 142 from extending too far from the tip 106. The grip 150 may allow for engagement of the retractable shaft 142, so as to properly move the retractable shaft 142. The rod 148 may connect the stopper 144 or the engagement portion 146 to the grip 140. The retractable shaft 142 may also be made magnetizable by including a magnet 146 disposed on or within the retractable shaft 142. The magnetic field or magnetic gradient may be removed or deactivated, such as by removing the magnet 146 or turning off an electromagnet. The target analyte-particle complex is no longer attracted and held to the retractable shaft 142 causing the target analyte-particle complex to remain within the liquid in the main body 102. The picker 140 may also include a light source 130, such as an LED, to illuminate an area in which the target analyte may be present. The light source 130 may be located anywhere along the main body 102, including the back end 104 and the tip 106. When the light source 130 is located at the back end 104, the main body 102 may be composed of a material capable of propagating or transmitting a light signal produced by the light source 130, such that the light signal exits at the tip 106 to illuminate the desired area. The light source 130 may be connected to a power supply (not shown), such as a battery, to supply current or power.

Alternatively, the retractable shaft 142 may be magnetized by an electromagnet, such as a coil wrapped around a segment of or the entire retractable shaft 142. Alternatively, the picker 140 may include a pump (not shown), such as a vacuum pump, a lead screw, or a hand pump with a wheel, to aid in providing the force for moving, removal, or isolation.

FIG. 2A shows an example picker 200, FIG. 2B shows a cross-sectional view of the example picker 200 taken along the line I-I. The picker 200 includes a piston 202, a pump block 204, and a cannula 208. The picker 200 may also include a fitting 206 with a first side 218 and a second side 220. The piston 202 includes a first end 210 and a second end 212. The cannula 208 includes an adapter 214 and a tube end 216, the tube end 216 including an opening 224. The first side 218 of the fitting 206 mates with the pump block 204, such as by a press-fit, detents, notches, complementary threads, or the like. A seal 222 may be formed between the first side 218 of the fitting 206 or the adapter 214 of the cannula 208 and the pump block 204, such as by an O-ring or silicone grease, to close the picker 200. The adapter 214 of the cannula 208 may mate with the second side 220 of the fitting 206 or a side of the pump block 204, such as by a press-fit, detents, notches, complementary threads, or the like.

The piston 202 may be any appropriate length. The second end 212 of the piston 202 may be located within the pump block 204, within the fitting 206, or may extend through the pump block 204 and into the adapter 214 of the cannula or past the adapter 214 of the cannula 208 and into the tube end 216 of the cannula. The first end 210 of the piston 202 may be located within the pump block 204 or extend out of a side of the pump block 204 opposite a side of the pump block 204 that connects to the adapter 214. The piston 202 and the cannula 208 may substantially share a central axis. The positioning of the piston 202 relative to the cannula 208 reduces or eliminates dead volume. Alternatively, the cannula 208, without the inclusion of the fitting 206, may be connected directly to the pump block 204. The adapter 214 may be connected to the first end of the pump block 204.

The pump block 204 at least partially houses the piston 202 and allows for translation of the piston 202 relative to the pump block 204, The piston 202, such as a lead screw or rod, translates within the pump block 204 to create a pressure differential at the tube end 216 of the cannula 208 so as to draw a target analyte into or expel the target analyte from the tube end 216 of the cannula 208. Moving the piston 202 upwards within the pump block 204 may create a negative pressure at the tube end 216 so as to draw a target analyte from the suspension into the cannula 208 or may create a positive pressure to expel a target analyte located within the cannula 208 from the tube end 216. The piston 202 may be connected to a motor or an actuator to drive the piston 202 up and down, thereby creating the desired pressure differential. The pump block 204 may include a complementary mating feature, such as threads or a bore, to accept and mate with the piston 202. When the piston 202 and the pump block 204 include complementary threads, the piston 202 may be rotated to cause the desired translation. A full rotation of the piston 202 may include any number of steps, including 1-10,000 steps. Those steps may then include any number of micro-steps, including 1-10,000 micro-steps. Each step or micro-step may draw in a volume approximately equal to or less than 1 picoliter, 10 picoliters, 100 picoliters, 1 nanoliter, 1 microliter, or 1 milliliter.

The cannula 208 may be primed with a fluid, such as a solution, an oil, a liquid metal, a buffer, or the like. Priming the picker 200 with the fluid provides better control than a picker that is not primed (i.e. filled with air). The air in a non-primed picker provides more disconnect between the piston 202 and a sample or the target analyte because of the greater compressibility of the air relative to the fluid. The greater compressibility leads to greater lag or delay, thereby providing less control and/or volume resolution. Furthermore, the opening 224 may be less than or equal to 1 micrometer or less than or equal to 1 millimeter.

The picker 200 may introduce a magnetic gradient as well, such as by a permanent magnet or an electromagnet, as shown in FIGS. 1B and 1C, respectively, whereby the cannula 208, the priming fluid, or a tip is magnetizable so as to propagate the magnetic gradient. The permanent magnet may be located along the tube end of the cannula, on the piston, or anywhere on the picker tip. When a ferrofluid primes the cannula, the permanent magnet may be located near the adapter. The electromagnet includes a coil, a first lead, a second lead, and a power supply, such as a battery. The coil wraps around the tube end of the cannula or the picker tip. A first end of the first lead is connected to the power supply and a second end of the first lead is connected to a first end of the coil. A first end of the second lead is connected to the power supply and a second end of the second lead is connected to a second end of the coil. The power supply is disposed outside of the pump block.

FIG. 2C shows a picker 230. The picker 230 is similar to the picker 200 except that the picker 230 includes a light source 232. The light source 232 produces a light signal that is propagated or transmitted by the cannula 208 or picker tip inserted into the cannula 208. The cannula 208 or the picker tip may be composed of a material capable of propagating or transmitting the light signal produced by the light source 232, such that the light signal exits at the tube end 216 of the cannula 208 or the end of the picker tip furthest away from the pump block 204 to illuminate the desired area and/or stimulate a fluorescent probe bound to a target analyte. When the light source 232, such as an LED, originates at a location other than the tube end 216 of the cannula 208 or the end of the picker tip furthest away from the pump block 204, a cable 234, such as a fiber optic cable, may transmit the light signal to the tube end 216 of the cannula 208 or the end of the picker tip furthest away from the pump block 204 for illumination and/or stimulation purposes. The light source 232 may provide oblique illumination. The light source 232 may be connected to a power supply (not shown), such as a battery, to supply current or power. Alternatively, the light source 232 may be between the top of the adapter of the cannula 208 and the fitting 206. Alternatively, at least one light source may be embedded in the tube end of the cannula 208. Alternatively, the light source 232 may be located on the adapter 214 or the pump block 204.

Figure 3:
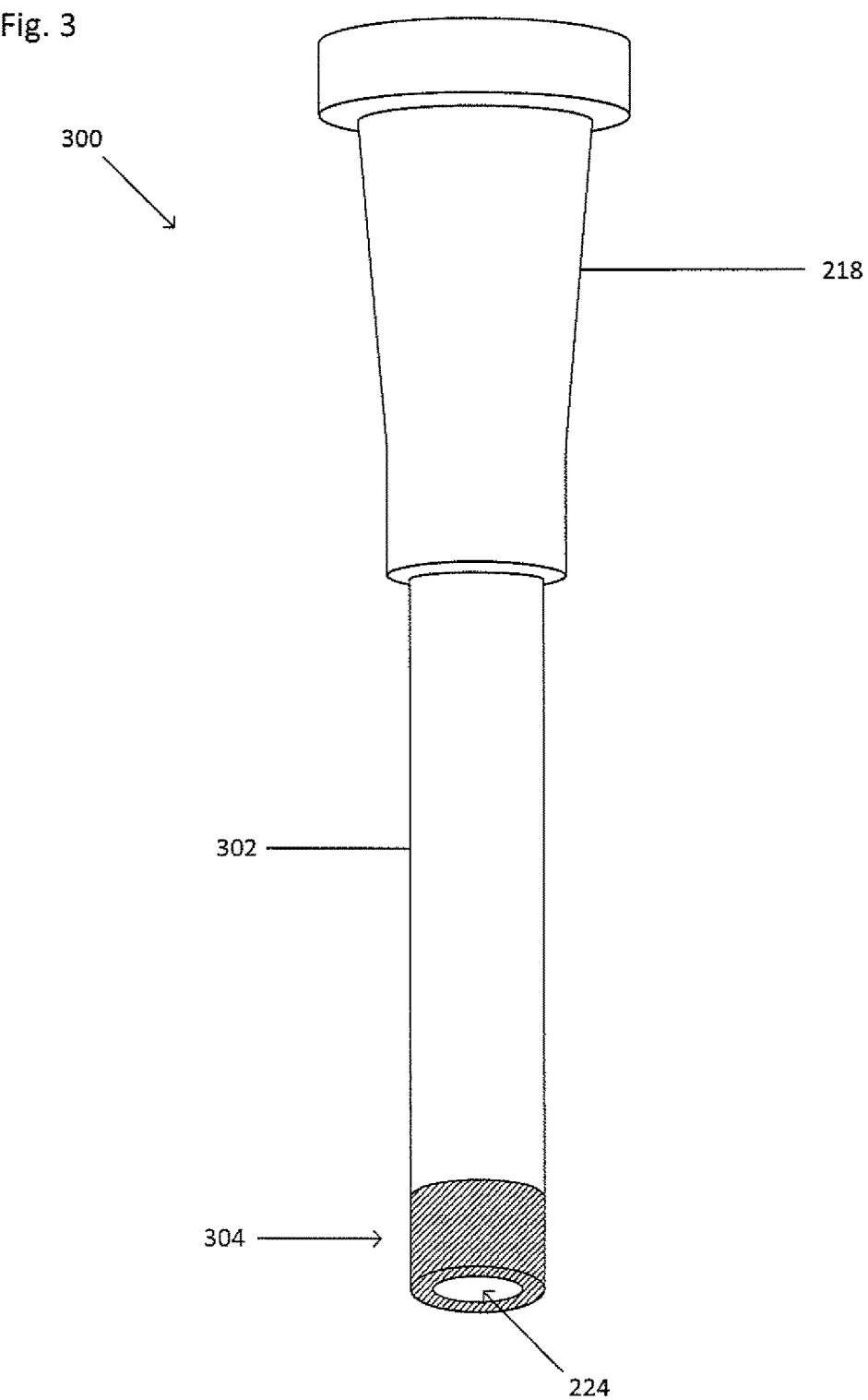
FIG. 3 shows an example cannula with a fluorescent tip.

FIG. 3 shows a cannula 300. The cannula 300 is similar to the cannula 208, except that a tube end 302 of the cannula 300 includes a fluorescent tip 304. The fluorescent tip 304 emits light in a particular wavelength when excited or stimulated by a stimulus, such as light with a first wavelength. The fluorescent tip 304 may be used to emit light that improves visualization of the cannula 300 for better placement over the desired target analyte during collection. Alternatively, the entire tube end 302 of the cannula 300 may be composed of a fluorescent material.

FIG. 4A shows a picker tip 400. FIG. 4B shows a cross-sectional view of the picker tip 400 taken along the line II-II. The picker tip 400 may be inserted into the tube end 216 of the cannula 208. The picker tip 400 includes a main body 402 and a permeable membrane 410. The main body 402 includes a first end 404 with a first bore 412 having a first diameter and a second end 406 with a tapered bore 414 having a second diameter which tapers to the same diameter as the first diameter of the first bore 412. The second end 406 may be entirely fluorescent or a portion thereof may be fluorescent, or the second end 406 may not be fluorescent. The second diameter may be larger or smaller than the first diameter. Furthermore, the widest part of the tapered bore 414 may be less than or equal to 1 micrometer or less than or equal to 1 millimeter.

The first end 404 is inserted within the tube end 216 of the cannula 208. The permeable membrane 410 may be located within the first bore 412 or the second bore 414 and is composed of a material including at least one pore. The permeable membrane 410 permits the target analyte to be drawn a distance into the picker. The picker tip 400 may also include a ridge 408 extending circumferentially from the main body 402 to prevent the picker tip 400 from translating further into the tube end 216 of the cannula 208.

FIG. 5 shows a picker tip 500. The picker tip 500 may be inserted into the tube end 216 of the cannula 208. The picker tip 500 includes a first end 502, a second end 504, and a central bore 506. The first end 502 is the portion of the picker tip 500 to be inserted into the tube end 216 of the cannula 208. The picker tip 500 may be straight, tapered, or a combination thereof. The central bore 506 extends from the first end 502 to the second end 504 and may be straight, tapered, or a combination thereof. Furthermore, the portion of the central bore 506 at the second end 504 may be less than or equal to 1 micrometer or less than or equal to 1 millimeter.

Magnified view 508 shows the second end 504 with an outer segment removed to reveal the inner configuration of the second end 504. The second end 504 may be flat or angled. The second end 504 may also include a counter-sink, as shown in FIG. 5.

Figure 6B:
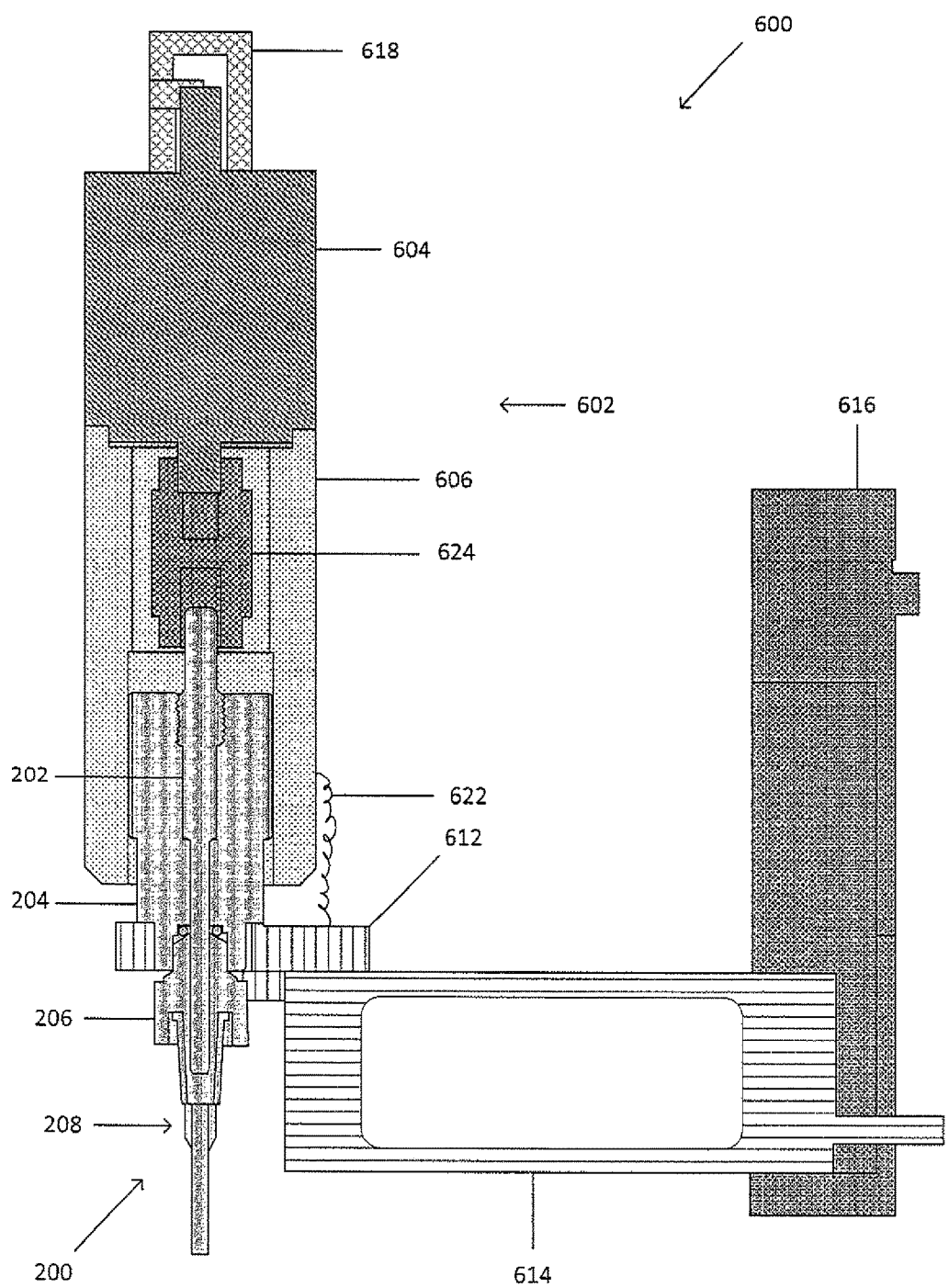

FIG. 6A shows picking system 600 including a drive assembly 602, the picker 200 as shown in FIGS. 2A-2B, and an actuator 614. FIG. 6B shows a cross-sectional view of the picking system 600. The drive assembly 602 includes a driver 604 including a first end and second end, a coupling 624 including a first end and a second end, and a housing 606. The first end of the coupling 624 mates with the second end of the driver 604, and the second end of the coupling 624 mates with the piston 202. When the second end of the driver 604 rotates, the coupling 624 rotates, thereby causing the piston 202 to rotate and translate within the pump block 204, the fitting 206, and the cannula 208. Alternatively, the second end of the driver 604 translates along a central axis, the coupling 624 translates along the central axis, thereby causing the piston 202 to translate within the pump block 204, the fitting 206, and the cannula 208.

The housing 606 is a piece which encases and protects at least the second end of the driver 604, the coupling 624, the first end 210 of the piston 202, and at least a portion of the pump block 204. The housing 606 may inhibit rotation of the driver 604 relative to the pump block 204. The housing 606 also supports the driver 604. The housing 606 may be fixedly attached to the driver 604. The housing 606 may include a travel slot (not shown) and a screw 610, such as a shoulder screw, to set the maximum permissible travel of the pump block 204 relative to the housing 604. The screw 610 is inserted through the travel slot (not shown) and screwed into a threaded hole on a side of the pump block 204. Alternatively, the screw 610 may be inserted through the travel slot (not shown) and compressed against a side of the pump block 204.

At least one side of the pump block 204 may be biased against at least one side of the housing 606 to inhibit rotational motion between the pump block 204 and the housing 606 so as to reduce or eliminate backlash. For example, a spring (not shown) may be placed between the pump block 204 and the housing 606 below the screw head of the screw 610.

The driver 604 may be a motor, such as a servomotor or a stepper motor, a piezo-electric actuator, a solenoid, or the like. The driver 604 provides high resolution control of the picker 200. The coupling 624 provides zero backlash and may be axially stiff and torsionally stiff. For example, the coupling 624 may be a non-expanding bellows or split-beam drive assembly, or the like.

The housing 606, by supporting the driver 604 and only encasing a portion of the driver 604, may reduce or eliminate expansion of the picker 200 that may result from the heat generated by the driver 604. Decoupling or separating the picker 200 and the driver 604 may reduce or eliminate expansion of the components of the picker 100. Furthermore, the weight of the driver 604 and external constraints 622, such as springs or weights, bias and preload the threads of the piston 202 to reduce or eliminate change or backlash. When the external constraints 622 are springs, the springs may extend from the housing 606 to a base 612. When the external constraints 622 are weights, the weights may be placed on top of the driver 604 or the housing 606.

The drive assembly 602 may also include a home switch 608 to return the picker 200 to the home or original position. The drive assembly 602 may also include a driver knob 618 for manual operation and/or wire leads 620 for automated operation. Manual operation may include adjustments or movements to the picker or picking system by hand or may include motorized adjustments or movements to the picker or picking by an operator via a manual controller, such as a touch screen, a joystick, a directional pad or the like.

The picking system 600 also includes the actuator 614, such as a piezo-electric actuator, a lead screw, or a stage. The actuator 614 may be connected to the picker 200, such as by the base 612, or may be connected to the drive assembly 602. The base 612 supports the picker 200 and may connect the actuator 614 to the picker 200. The base 612 may include a light source (not shown), such as a LED, to provide oblique illumination of the picker tip or tube end of the cannula.

The actuator 614 provides high resolution location control of the picker 200, has a rapid response (for example, to allow for oscillation), and may be operated in an open or closed loop. The actuator 614 may provide motion along the x, y, and z axes or may provide motion along only one axis. The actuator 614 may have a travel range of 1 nanometer to more than 50 millimeters along each axis. The lower end of the travel range permits the actuator 614 to make finer adjustments (approximately 0.001-500 μm) for the picker 200 so as to better locate and pick a target analyte. The upper end of the travel range permits the actuator to make coarser adjustments (approximately 10-50 mm) for the picker 200, such as to move the picker to different wells to draw up or expel different fluids from the different wells or receptacles, to change cannulas or replace parts when it is desirous to do so. The cannula or picker tip, for example, may be replaced by manual operation (i.e. changing out by hand) or by automated operation (i.e. by expelling the used cannula or picker tip, moving the picker over a cartridge containing at least one new cannula or picker tip, lowering the picker to mate with the new cannula or picker tip, raising the picker, and returning to a desired position). When the actuator 614 provides motion along only one axis, a second actuator (not shown) may be used to provide motion along all three axes. Furthermore, when the actuator 614 provides motion along only one axis, the second actuator (not shown) may be used for coarser adjustments, whereas the actuator 614 may be used for finer adjustments.

The picking system 600 may also include a mount 616 to attach the picker 200, the drive assembly 602, and the actuator 614 to an imaging or detection system, such as a scanner or a microscope. The mount 616 may be stationary within the imaging or detection system or may be attached to the second actuator (not shown) within the imaging or detection system.

The picker can be composed of a variety of different materials including, but not limited to, ceramics; glass; metals; organic or inorganic materials; plastic materials; and combinations thereof. The picker tip can also be composed of a variety of different materials including, but not limited to, ceramics; glass; metals; organic or inorganic materials; plastic materials; and combinations thereof. Furthermore, the cannula or the picker tip may be composed of a material that is fluorescent. Additionally, the tube end of the cannula or the picker tip may be impact-resistant, hard, and dimensionally stable (i.e. axially and/or torsionally stiff).

The permanent magnet includes, but is not limited to, a ring magnet, a bar magnet, a horseshoe magnet, a donut-shaped magnet, a spherical magnet, a polygon-shaped magnet, a polyhedral shape, a wand magnet, a kidney-shaped magnet, a trapezoidal magnet, a disk magnet, a cow magnet, a block or brick magnet, or combinations thereof. The magnetizable material includes, but is not limited to, metals, organic materials, inorganic materials, minerals, ferrofluids, and combinations thereof.

The cannula, tip and engagement portion may be stiff, flexible or formable. The cannula, tip and engagement portion may be straight, angled, curved, hooked, or any appropriate shape or configuration. The cannula, tip, and engagement portion may be non-clogging.

FIG. 7 shows a picking system 700 including the picking system 600 and a stage 702. The picking system 600 may be attached to a mount 708. The stage 702 may be attached to an actuator 704 to move the stage 702 along at least one axis. Alternatively, the stage 712 may be attached to multiple actuators, each actuator configured to move the stage 712 along at least one axis. The stage 702 may be attached directly to a mount 706 or indirectly to the mount 706 via the actuator 704, so as to attach the stage 702 to the same imaging or detection device as the picking system 600.

Methods for Using a Picker

Figure 8:
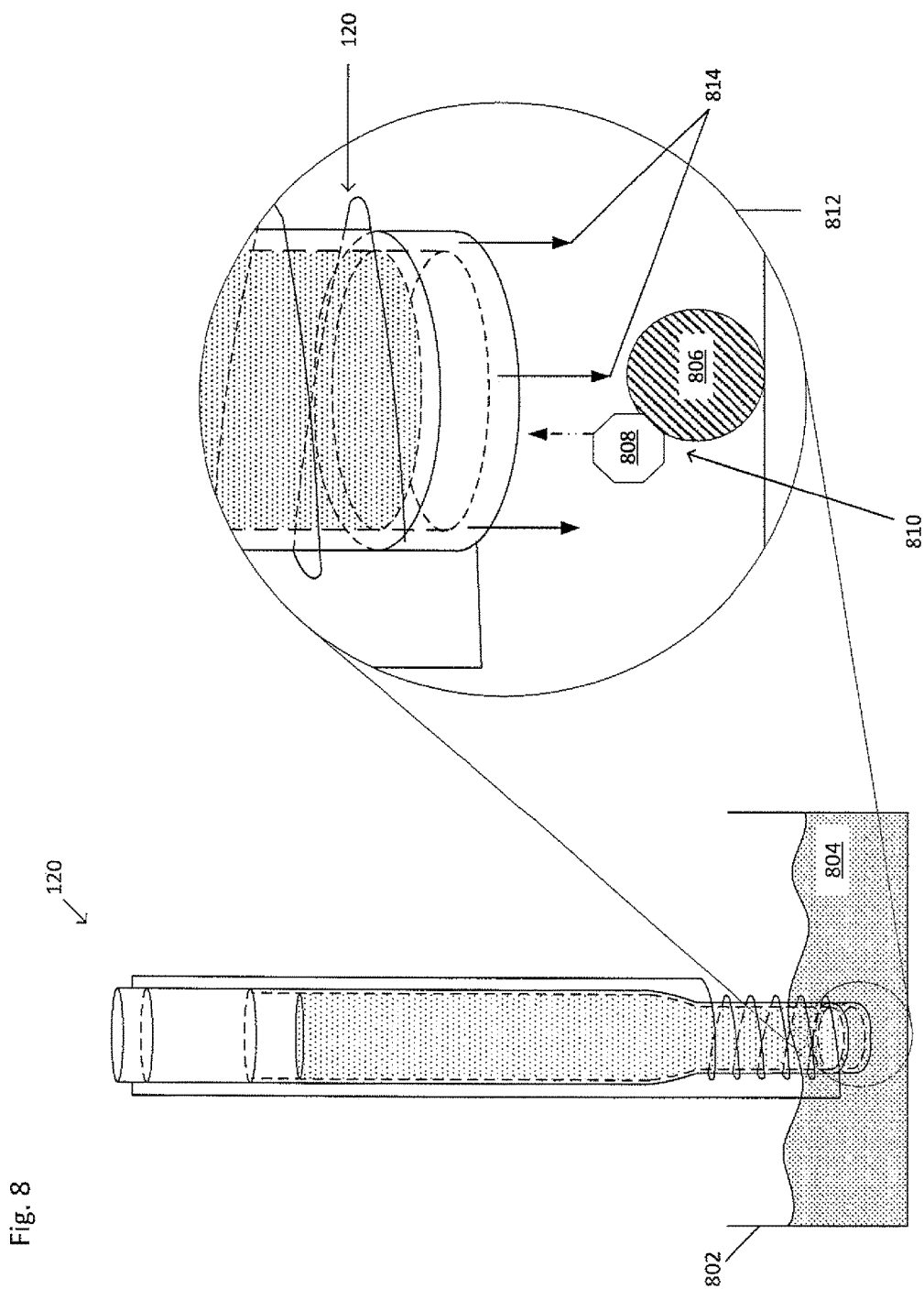
FIG. 8 shows isolation of target analyte using a picker.

A picker may be used to isolate a target analyte from a suspension. For example, FIG. 8 shows the picker 120 isolating a target analyte 806 from a suspension 804. A solution containing a particle 808 to conjugate with the target analyte 806 to form a target analyte-particle complex 810 may be added to the suspension 804. The target analyte-particle complex 810, including the particle 808 and the target analyte 806, being attracted by a magnetic field introduced by the picker 120, moves upwards within a vessel 802. The particle 808 which is bound to the target analyte 806 causes the target analyte 806 to move upwards toward the picker 120. The target analyte 806 may then be held, via the particle 808 to which the target analyte 806 is bound, to the picker 120 due to the magnetic field. Alternatively, the target analyte-particle complex 210 may be attracted to the picker 120 via the magnetic force and then sucked into the picker 120 via a suction device on the picker 120.

The particle may come in any form, including, but not limited to, a bead, a nanoparticle (such as a quantum dot), a shaving, a filing, or the like, such that the particle is capable of being attracted by a magnetic field or magnetic gradient introduced by a magnet. The particle may itself be magnetic, diamagnetic, ferromagnetic, or paramagnetic.

The picker may be used in conjunction with a vessel 802, such as a well, a well plate, a slide, or the like. For example, to isolate the target analyte 806, the suspension 804 suspected of containing the target analyte 806 can be placed in the vessel 802. Alternatively, a fraction of the suspension 804, the fraction suspected of containing the target analyte 806, can be placed in the vessel 802. The vessel 802 may be imaged to detect the target analyte 806 and determine the location of the target analyte 806. After determining the location of the target analyte 806, the target analyte 806 may be manipulated and/or isolated by the introduction of a force to draw the target analyte 806 to or into a picker, such as a manipulator 120. The picker 120 can be brought into close proximity to the specific target analyte. The force produced by the picker 120 attracts, moves, or holds specific target analyte, so that the target analyte may be manipulated as desired. For example, the picker 120 produces the force by electromagnetism. When a suction or vacuum force is used, the target analyte 806 may be pulled out of the vessel 802. The solid arrows 814 show the light signal produced by the light source 130 illuminating the area in which the target analyte 806 is located.

To remove the target analyte from a wet mount or a suspension, a pressure gradient may be introduced by the picker 200 after the cannula 208 is placed near, over, or above the target analyte. The pressure gradient causes the target analyte to move into the cannula 208. To remove the target analyte from a dry mount (i.e. a dry slide), the cannula 208 is placed over the target analyte. The cannula 208 may then be moved horizontally or orthogonally to detach the target analyte from the mount. The pressure gradient may then be introduced to draw the target analyte into the cannula 208. Alternatively, the cannula 208, after being placed over the target analyte, may oscillate up and down at any appropriate frequency to detach the target analyte from the mount, such as, for example, less than or equal to approximately 10 kHz. The pressure gradient may then be introduced to draw the target analyte into the cannula 208. Alternatively, the cannula 208 may be placed over the target analyte and the target analyte may be held within the cannula without actively applying the pressure gradient. Alternatively, the cannula 208 may be placed over the target analyte and dragged across the surface of the slide, thereby dislodging the target analyte and causing the target analyte to be held within the cannula without actively applying the pressure gradient. Alternatively, the permanent magnet or electromagnet may be engaged and/or activated so as to remove a target analyte bound to a magnetic particle.

The target analyte may be collected, and once collected, the target analyte may be analyzed using any appropriate analysis method or technique, though more specifically intracellular analysis including intracellular or extracellular protein labeling; nucleic acid analysis, including, but not limited to, protein or nucleic acid microarrays; FISH; or bDNA analysis. These techniques require isolation, permeabilization, and fixation of the target analyte prior to analysis. Some of the intracellular proteins which may be labeled include, but are not limited to, cytokeratin ("CK"), actin, Arp2/3, coronin, dystrophin, FtsZ, myosin, spectrin, tubulin, collagen, cathepsin D, ALDH, PBGD, Aka1, Akt2, c-myc, caspases, survivin, $p27^{kip}$, FOXC2, BRAF, Phospho-Akt1 and 2, Phospho-Erk1/2, Erk1/2, P38 MAPK, Vimentin, ER, PgR, PI3K, pFAK, KRAS, ALKH1, Twist1, Snail1, ZEB1, Slug, Ki-67, M30, MAGEA3, phosphorylated receptor kinases, modified histones, chromatin-associated proteins, and MAGE. In order to fix, permeabilize, or label, fixing agents (such as formaldehyde, formalin, methanol, acetone, paraformaldehyde, or glutaraldehyde), detergents (such as saponin, polyoxyethylene, digitonin, octyl β-glucoside, octyl β-thioglucoside, 1-S-octyl-β-D-thioglucopyranoside, polysorbate-20, CHAPS, CHAPSO, (1,1,3,3-Tetramethylbutyl)phenyl-polyethylene glycol or octylphenol ethylene oxide), or labeling agents (such as fluorescently-labeled antibodies, Pap stain, Giemsa stain, or hematoxylin and eosin stain) may be used.

It should be understood that the method and system described and discussed herein may be used with any appropriate suspension or biological sample, such as blood, bone marrow, cystic fluid, ascites fluid, stool, semen, cerebrospinal fluid, nipple aspirate fluid, saliva, amniotic fluid, vaginal secretions, mucus membrane secretions, aqueous humor, vitreous humor, vomit, and any other physiological fluid or semi-solid. It should also be understood that a target analyte can be a cell, such as ova or a circulating tumor cell ("CTC"), a nucleated red blood cell, a fetal cell, a circulating endothelial cell, a vesicle, a liposome, a protein, a nucleic acid, a biological molecule, a naturally occurring or artificially prepared microscopic unit having an enclosed membrane, a parasite, a microorganism, or an inflammatory cell.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

We claim:

1. A picker comprising:
   a pump block comprising a first end and a second end comprising a seal,
   a piston at least partially housed within the pump block and partially extending through the seal, wherein the piston translates relative to the pump block, and wherein one end of the piston extends into a cannula, and
   the cannula comprising an adapter end and a tube end, wherein the adapter end is connected to the second end of the pump block and the tube end extends away from the pump block, and
   a housing to encase at least a portion of the pump block and the one end of the piston extending into the cannula.

2. The picker of claim 1, further comprising:
   a driver; and
   a coupling mating the driver to the piston.

3. The picker of claim 2, wherein the housing is also to encase the coupling and at least a portion of the driver.

4. The picker of claim 3, wherein at least one side of the pump block is biased against at least one side of the housing to inhibit rotational motion between the pump block and the housing to reduce or eliminate backlash.

5. The picker of claim 3, further comprising at least one weight on top of the driver or the housing to the base to bias and preload threads of the piston to reduce or eliminate backlash.

6. The picker of claim 2, wherein the coupling provides zero backlash and is axially and torsionally stiff.

7. The picker of claim 2, wherein the coupling is a non-expanding bellows or a split-beam drive assembly.

8. The picker of claim 1, further comprising a mount connecting the picker to an imaging or detection device.

9. The picker of claim 1, further comprising a light source.

10. The picker of claim 1, wherein a full rotation of the piston includes 1-10,000 steps.

11. The picker of claim 10, wherein each step includes 1-10,000 micro-steps.

12. The picker of claim 11, wherein each step or micro-step equates to a volume equal to or less than 1 picoliter, 10 picoliters, 100 picoliters, 1 nanoliter, 1 microliter, or 1 milliliter.

13. A system comprising:
    a picker comprising
        a pump block comprising a first end and a second end comprising a seal,
        a piston at least partially housed within the pump block and partially extending through the seal, wherein the piston translates relative to the pump block, and
        a cannula comprising an adapter end and a tube end, wherein the adapter end is connected to the second end of the pump block and the tube end extends away from the pump block, wherein one end of the piston extends into the cannula; and
    a stage to support a substrate or a sample from which the picker may isolate a target analyte or a portion of the sample.

14. The system of claim 13, further comprising an actuator to move the stage along at least one of the x-, y-, or z-axes.

15. The system of claim 14, further comprising a mount connecting the picker to an imaging or detection device.

16. The system of claim 15, further comprising a mount to connect to the actuator to attach the stage to the imaging or detection system.

17. The system of claim 13, further comprising an actuator to move the picker along at least one of the x-, y-, or z-axes.

18. The system of claim 17, further comprising a mount connecting the stage to an imaging or detection device.

19. The system of claim 18, further comprising a mount to connect to the actuator to attach the picker to the imaging or detection system.

20. The system of claim 13, the picker further comprising:
    a driver; and
    a coupling mating the driver to the piston.

21. The system of claim 20, the picker further comprising a housing to encase at least a portion of the driver, the coupling, a first end of the piston, and at least a portion of the pump block.

* * * * *